(12) United States Patent
Durham et al.

(10) Patent No.: US 10,688,291 B2
(45) Date of Patent: *Jun. 23, 2020

(54) MEDICAL SKIN APPLICATOR APPARATUS

(71) Applicant: ZUREX PHARMA, INC., Middleton, WI (US)

(72) Inventors: Carmine J. Durham, Madison, WI (US); R. Andrew Morgan, Middleton, WI (US); Dawn Parks, Sun Prairie, WI (US); Michael Kvalo, Portage, WI (US)

(73) Assignee: ZUREX PHARMA, INC., Middleton, WI (US)

( * ) Notice: Subject to any disclaimer, the term of this patent is extended or adjusted under 35 U.S.C. 154(b) by 253 days.

This patent is subject to a terminal disclaimer.

(21) Appl. No.: 15/834,993

(22) Filed: Dec. 7, 2017

(65) Prior Publication Data

US 2018/0099132 A1  Apr. 12, 2018

Related U.S. Application Data

(63) Continuation of application No. 14/251,194, filed on Apr. 11, 2014, now Pat. No. 9,844,654.

(60) Provisional application No. 61/813,953, filed on Apr. 19, 2013.

(51) Int. Cl.
  *A61F 13/40* (2006.01)
(52) U.S. Cl.
  CPC ................. *A61M 35/006* (2013.01)
(58) Field of Classification Search
  CPC ........... A61M 35/006; A61M 35/003
  See application file for complete search history.

(56) References Cited

U.S. PATENT DOCUMENTS

| | | |
|---|---|---|
| 4,415,288 A | 11/1983 | Gordon et al. |
| 4,925,327 A | 5/1990 | Wirt et al. |
| 5,769,552 A | 6/1998 | Kelley et al. |
| 5,791,801 A | 8/1998 | Miller |
| 6,505,985 B1 | 1/2003 | Hidle |
| 6,910,822 B2 | 6/2005 | Hidle |
| 6,978,945 B2 | 12/2005 | Wong |
| 7,614,811 B2 | 11/2009 | Kaufman et al. |
| 7,866,471 B2 | 1/2011 | Callahan |
| 7,866,907 B2 | 1/2011 | Cable |
| 8,113,731 B2 | 2/2012 | Cable |
| 8,118,766 B2 | 2/2012 | Davis |
| 8,348,537 B2 | 1/2013 | Cable |
| 9,629,990 B2 | 4/2017 | Law |
| 2002/0012563 A1 | 1/2002 | May et al. |
| 2002/0076258 A1 | 6/2002 | Crosby et al. |
| 2004/0068218 A1 | 4/2004 | Davis et al. |

(Continued)

FOREIGN PATENT DOCUMENTS

| | | |
|---|---|---|
| WO | 2010/078363 | 7/2010 |
| WO | 2011/018622 | 2/2011 |

OTHER PUBLICATIONS

European Search Report, EP Patent Application No. 14785340.2, dated Nov. 21, 2016.

*Primary Examiner* — Susan S Su
(74) *Attorney, Agent, or Firm* — Casimir Jones, SC; Robert A. Goetz

(57) ABSTRACT

The present invention relates to a fluid applicator apparatus and methods of using the apparatus. In particular, the present invention relates to an apparatus for storing and dispensing solutions (e.g., fluid solutions of any kind) (e.g., liquid medicaments and/or sterilization solutions) to a surface of a subject.

13 Claims, 3 Drawing Sheets

(56) References Cited

U.S. PATENT DOCUMENTS

| | | |
|---|---|---|
| 2004/0162533 A1 | 8/2004 | Alley |
| 2006/0018701 A1 | 1/2006 | Mohiuddin |
| 2007/0147946 A1 | 6/2007 | Cybulski |
| 2007/0276312 A1 | 11/2007 | Davis |
| 2007/0293831 A1 | 12/2007 | Kwochka |
| 2010/0168638 A1 | 7/2010 | Korogi |
| 2012/0219346 A1 | 8/2012 | Law |
| 2015/0290081 A1 | 10/2015 | Kropczynski | ns # MEDICAL SKIN APPLICATOR APPARATUS

CROSS-REFERENCE TO RELATED APPLICATIONS

The present application is a continuation of U.S. patent application Ser. No. 14/251,194, filed Apr. 11, 2014, allowed as U.S. Pat. No. 9,844,654, which claims priority to U.S. Provisional Patent Application No. 61/813,953, filed Apr. 19, 2013, the contents of which are incorporated by reference in their entireties.

FIELD OF THE INVENTION

The present invention relates to a fluid applicator apparatus and methods of using the apparatus. In particular, the present invention relates to an apparatus for storing and dispensing solutions (e.g., fluid solutions of any kind) (e.g., liquid medicaments and/or sterilization solutions) to a surface of a subject.

BACKGROUND OF THE INVENTION

Many medical procedures involve application of medicines, sterilizing fluids, antiseptics, gels, agents or other materials to portions of the body, such as the skin, for preparation, treatment, etc. Such medicines, sterilizing fluids, agents are typically transferred to the skin via an applicator. Conventional liquid applicators incorporate a glass ampoule or plastic blow-molded bottles for storing the liquid and a mechanism for fracturing the ampoule to release the stored liquid. The released liquid contacts a swab, foam pad or tip for application to the skin.

However, numerous problems are encountered with applicators of this type. For example, the design of most conventional liquid applicators is prone to unintentional actuation (e.g., release of the fluid). Therefore, it would be desirable to overcome the disadvantages and drawbacks of the prior art with a body surface applicator that decreases the risk of unintentional actuation.

SUMMARY OF THE INVENTION

The present invention relates to a fluid applicator apparatus and methods of using the apparatus. In particular, the present invention relates to an apparatus for storing and dispensing solutions (e.g., fluid solutions of any kind) (e.g., liquid medicaments and/or sterilization solutions) to a surface of a subject.

Embodiments of the present invention provide apparatuses and methods of using such apparatuses to apply solutions to a surface of a subject. The apparatuses overcome problems of existing devices by preventing accidental, undesired, dispensing of solutions.

For example, in certain embodiments, the present invention provides medical applicator apparatuses. The present invention is not limited to particular types of medical applicator apparatuses. In some embodiments, the apparatus (as shown in FIGS. 1, 2, 3 and 5) have a main body, and an applicator component.

Such apparatuses are not limited to a particular type of main body. In some embodiments, the main body serves as the main portion of the apparatus, serves as a housing for a fluid housing, serves as a channel through which a fluid can pass, and serves as a conduit between a flowing fluid and the applicator. In some embodiments, the main body has a main body proximal end (having a main body proximal end rim), a main body mid portion, and a main body distal end.

The main body is not limited to particular size dimensions. In some embodiments, the size of the main body is such that it is able to house a fluid housing (e.g., fluid container) (described in more detail below). The main body is not limited to a particular shape or design. In some embodiments, the shape of the main body is such that it may be comfortably handled and/or gripped by a user (e.g., a human user).

Such apparatuses are not limited to a particular type of applicator component. In some embodiments, the applicator component serves as the portion of the apparatus that receives a fluid (from the main body) and emits the fluid in a desired manner (e.g., onto a subject). In some embodiments, the apparatus engages the main body at the main body distal end.

The applicator may be any material suitable for absorbing and applying a solution (e.g., medicament or sterilization solution) to the skin of an animal. Examples include, but are not limited to, sponges, absorbent pads, and the like.

In some embodiments, the main body has an opener element positioned within the interior of the main body at the main body mid portion. In some embodiments, the opener element is a protuberance that is configured to actuate (e.g., open) (e.g., insert into) an operable door within a fluid housing (described in more detail below). In some embodiments, the opener element is triangular in shape and rigidly positioned within the interior of the main body at the main body mid portion. In some embodiments, the opener element has a pointed front end angled acutely so as to facilitate the actuating (e.g., opening) of an operable door (e.g., a fluid housing operable door), a top end shaped to facilitate the retention of such an operable door in an open position (described in more detail below), and a back end. In some embodiments, the top end is more acutely angled in comparison to the pointed front end thereby facilitating positioning of an opened fluid housing operable door on such top end (so as to retain the opened operable door in an open position). In some embodiments, the width of the opener element is sufficiently narrow so as to retain a hollow passage within the interior of the main body. In some embodiments, the width of the opener element is sufficiently narrow so as to facilitate (e.g., not hinder) the passage of a fluid through the interior of the main body to the applicator.

Such apparatuses are configured to house a fluid housing within the main body (as shown in FIGS. 3, 4 and 5). The present invention is not limited to particular types or kinds of a fluid housing. In some embodiments, the fluid housing is positioned within the interior of the main body from the main body proximal end to the vicinity of the main body mid portion just prior to the opener element. In some embodiments, the fluid housing has a closed fluid housing proximal end and a closed fluid housing distal end (e.g., thereby enabling the fluid housing to securely store a fluid). In some embodiments, the fluid housing is positioned within the main body such that the fluid housing proximal end does not extend beyond (outside the top of) the main body proximal end rim (thereby preventing unintentional actuation of the apparatus).

In some embodiments, the fluid housing distal end is closed with a fluid housing distal end operable door. The present invention is not limited to a particular type or kind of fluid housing distal end operable door. In some embodiments, the operable door is hinge based such that it is configured to be opened. In some embodiments, the operable door is peel hinge based such that it is configured to be opened. In some embodiments, the operable door has an operable door top peel portion and an operable door bottom peel portion. In some embodiments, the operable door top peel portion and the operable door bottom peel portion have different degrees of thickness. In some embodiments, the thickness of the operable door bottom peel portion is such that upon engagement with the opener element pointed front end the operable door bottom peel portion will detach (e.g., "break"). In some embodiments, the thickness of the operable door top peel portion is thick enough to bend (e.g., flex) without detaching as the operable door bottom peel portion detaches. As such, in some embodiments, the operable door is configured to open via detachment of the operable door bottom peel portion and flexing of the operable door top peel portion in response to engagement with the opener element pointed front end.

Accordingly, in some embodiments, depression of the fluid housing proximal end (e.g., by a user) causes the fluid housing to distally advance through the interior of the main body resulting in engagement between the fluid housing operable wall and the opener element. Such engagement between the fluid housing operable wall and the opener element results in contacting of the opener element pointed front end with the operable wall bottom peel portion such that the operable wall bottom peel portion (e.g., opens), and as the opener element advances into the fluid housing, the operable door top peel portion flexes and rests upon the opener element top end (thereby retaining the operable door in an open position). In some embodiments, such opening of the operable door results in a release of the fluid housing contents (e.g., fluid) through the opened operable door, into the interior of the main body (e.g., the main body mid portion and main body distal end), and ultimately into the applicator. In some embodiments, the entire contents of fluid housing are thereby transferred to the applicator, which may thereby be used to apply such contents to a subject. In some embodiments, the operable door top peel portion and the operable door bottom peel portion are formed through a coining process.

Similarly, in certain embodiments, the present invention provides apparatuses for applying a fluid, comprising a hollow main body having an open main body proximal end, a main body mid portion, and an open main body distal end, wherein the interior of the main body mid portion has therein an opener element, an applicator component, and a fluid housing having a closed fluid housing proximal end and a fluid housing distal end having a fluid housing operable door, wherein the fluid housing operable door has therein a bottom portion peeled element and a top portion peeled element, wherein the top portion peeled element is thicker than the bottom portion peeled element.

In some embodiments, the main body distal end is engaged with the applicator component. In some embodiments, the fluid housing is positioned within the interior of the main body such that the fluid housing operable door is positioned in the vicinity of the opener element such that a distal movement of the fluid housing will result in an actuating (e.g., opening) (e.g., insertion into) of the opener element into the fluid housing operable door thereby releasing the contents of the fluid housing into interior of the main body and into the applicator component.

In some embodiments, the actuating (e.g., opening) (e.g., insertion into) of the opener element into the fluid housing operable door involves a detachment of the bottom portion peeled element and a flexing of the top portion peeled element such that the operable door engages the opener element and remains open.

In some embodiments, the fluid housing is positioned within the interior of the main body such that the fluid housing proximal end is flush or recessed relative to the main body proximal end. In some embodiments, the fluid housing houses a fluid. In some embodiments, the fluid is a medicament fluid or a sterilizing fluid.

In some embodiments, the applicator component is an absorbent sponge or pad. In some embodiments, the applicator component has a shape selected from the group consisting of round, oval, square, triangular, and tear-drop.

In some embodiments, methods for applying a fluid to a subject utilizing such apparatuses are provided. For example, in some embodiments, such methods comprise contacting an apparatus of the present invention having fluid within the fluid housing with a surface of a subject; and causing actuating (e.g., opening) (e.g., insertion) of the opener element into the fluid housing operable door thereby evacuating the fluid within the fluid housing into the interior of the main body and through the applicator onto the surface of the subject.

Additional embodiments are described herein.

DEFINITIONS

As used herein, the term "proximal" refers to the portion of a structure that is closer to a user, while the term "distal" refers to the portion that is further from the user.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc. In some embodiments, non-human animals are mammals. In some embodiments, non-human animals are farm or agricultural animals (e.g., milk producing animals such as cows, sheep, goats, etc.)

As used herein, the term "practitioner" or "user" refers to any user of the apparatus of embodiments of the present invention. The "user" or "practitioner" can be a medical professional (e.g., veterinarian, doctor, nurse or other health care provider) or non-medical user (e.g., human (e.g., human patient) or human caretaker of a non-human animal).

DETAILED DESCRIPTION OF THE INVENTION

The present invention relates to a fluid applicator apparatus and methods of using the apparatus. In particular, the present invention relates to an apparatus for storing and dispensing solutions (e.g., fluid solutions of any kind) (e.g., liquid medicaments and/or sterilization solutions) to a surface of a subject.

The following discussion includes descriptions of the various embodiments of the applicator apparatus in accordance with the principles of the present disclosure followed by a description of uses of the apparatus.

Figure 1:
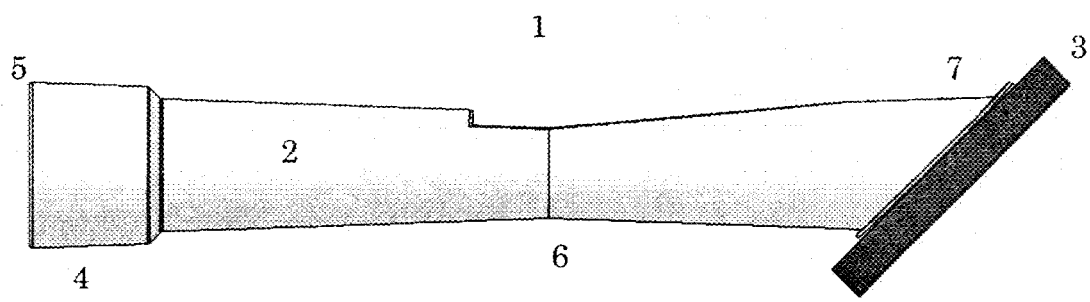
FIG. 1 shows a side view of an apparatus embodiment of the present invention.
Figure 2:
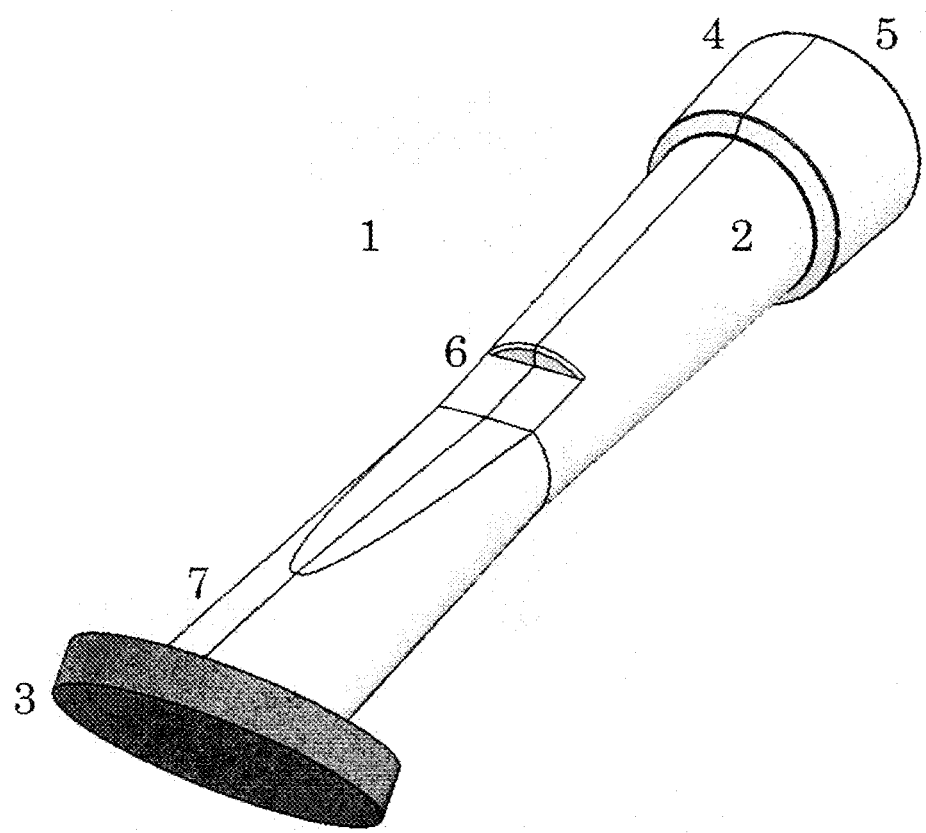
FIG. 2 shows a top down view of an apparatus embodiment of the present invention.

Referring to FIGS. 1-5, embodiments of the present invention provide medical applicator apparatuses. FIG. 1 shows a side external view of apparatus 1. As shown, the apparatus 1 comprises a main body 2 and an applicator component 3. FIG. 2 shows a top down view of the apparatus 1 wherein the main body 2 and applicator component 3 are visible.

Still referring to FIGS. 1 and 2, the main body 2 has a main body proximal end 4 (having a main body proximal end rim 5), a main body mid portion 6, and a main body distal end 7. The main body 2 is not limited to particular size dimensions. In some embodiments, the size of the main body 2 is such that it is able to house a fluid housing (e.g., fluid container) (described in more detail below). The main body 2 is not limited to a particular shape or design. In some embodiments, the shape of the main body 2 is such that it may be comfortably handled and/or gripped by a user (e.g., a human user). In some embodiments, the shape of the main body is generally cylindrical. In some embodiments, the main body proximal end 4 and main body distal end 7 are open ended thereby enabling the main body 2 to be a hollow passageway its distal and proximal ends.

Still referring to FIGS. 1 and 2, the applicator component 3 engages the main body 2 at the main body distal end 7. In some embodiments, the applicator component 3 is sized such that it closes the opening associated with the main body distal end 7. The applicator 3 is not limited to a particular manner of engagement with the main body distal end 7. In some embodiments, the applicator 3 engages with the main body distal end 7 with an adhesive. In some embodiments, the applicator 3 engages with the main body distal end 7 such that as the applicator 3 becomes saturated with a fluid it remains securely engaged with the main body distal end 7. In some embodiments, the applicator 3 engages with the main body distal end 7 such that as the applicator 3 becomes saturated with a fluid and is used to contact a subject (e.g., the skin of a subject) it remains securely engaged with the main body distal end 7.

The applicator 3 may be any material suitable for absorbing and applying a solution (e.g., medicament or sterilization solution) to the skin of an animal. Examples include, but are not limited to, sponges, absorbent pads, and the like. The applicator 3 is not limited to having a particular shape. In some embodiments, the applicator 3 is a circular or oval shape but may be any shape. For example, in some embodiments, different shapes or geometries of applicators are used for different applications (e.g., applications to different body parts or sizes of animals or subjects). In some embodiments, the applicator 3 is tear-drop shaped, square, oval, triangular, etc. The applicator 3 is not limited to particular size dimensions.

In use, in some embodiments, the applicator 3 is a multi-contoured absorbent member that conforms to substantially all body contours or topology of a subject. For example, a prow shaped nose facilitates application to eyes, ears, fingers, toes, groin, or other confined topology. Additionally, a contoured section conforms to the radial surface of an arm or leg of a subject.

Figure 3:
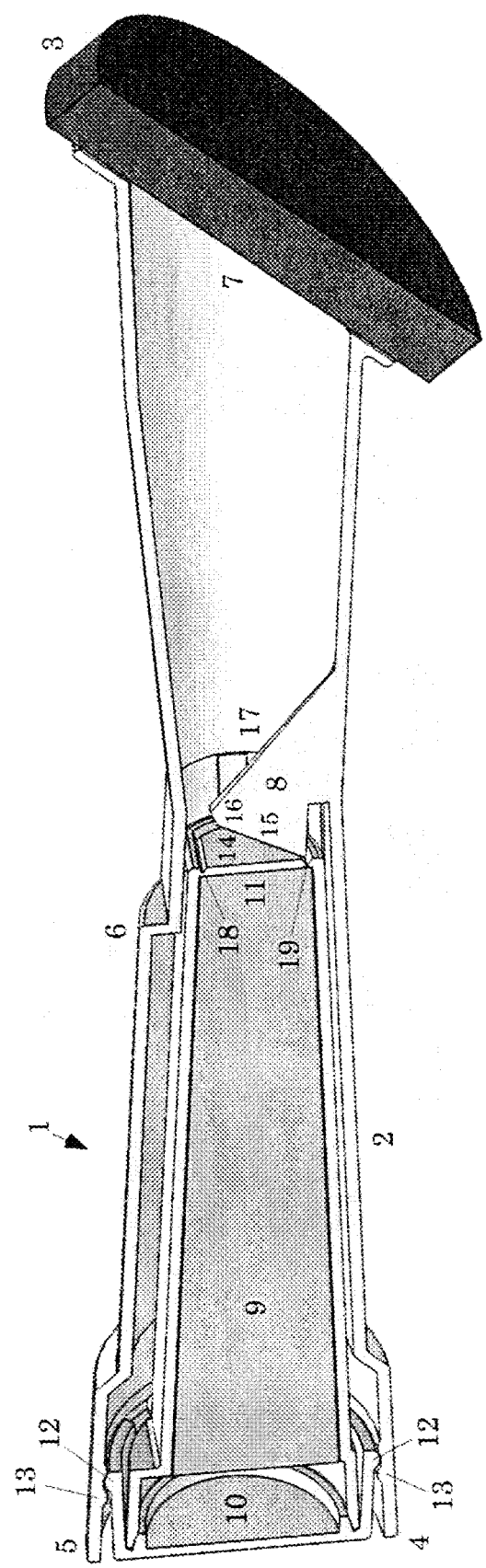
FIG. 3 shows a detailed cut out of the side of the apparatus embodiment of the present invention.

FIG. 3 shows a detailed cut out of the side of the apparatus 1 having the main body 2 and applicator component 3, along with the main body proximal end 4 (having a main body proximal end rim 5), main body mid portion 6, and main body distal end 7. As shown, an opener element 8 is positioned within the interior of the main body 2 at the main body mid portion 6.

The apparatus 1 is not limited to a particular type or kind of an opener element 8. In some embodiments, the opener element 8 is a protuberance that is configured to actuate (e.g., open) an operable door within a fluid housing (described in more detail below). The opener element 8 is not limited to particular size dimensions and/or shapes.

Figure 5:
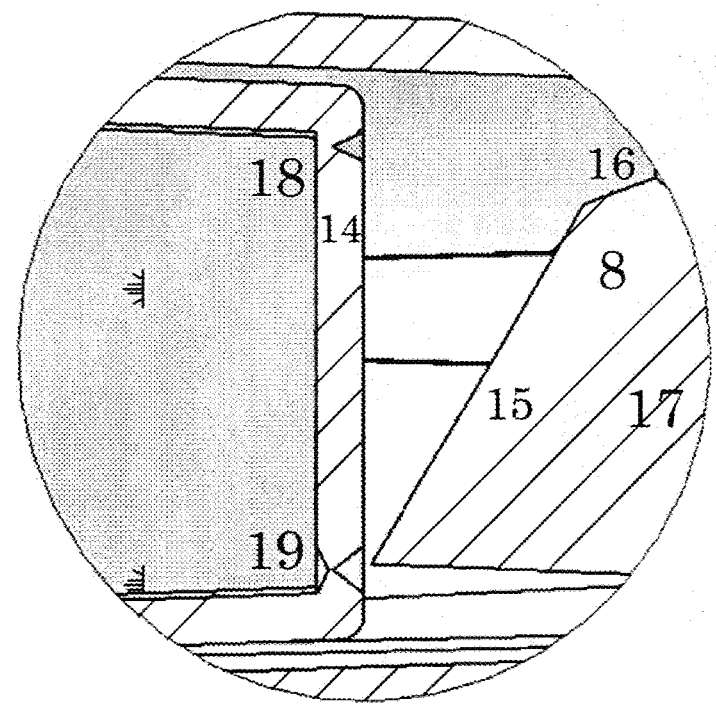
FIG. 5 shows a detailed view of the fluid housing distal end and the main body mid portion.

In some embodiments, as shown in FIGS. 3 and 5, the opener element 8 is triangular in shape and rigidly positioned within the interior of the main body 2 at the main body mid portion 6. In some embodiments, as shown in FIGS. 3 and 5, the opener element 8 has a pointed front end 15 angled acutely so as to facilitate the opening of an operable door (e.g., a fluid housing operable door), a top end 16 shaped to facilitate the retention of such an operable door in an open position (described in more detail below), and a back end 17. In some embodiments, as shown in FIGS. 3 and 5, the top end 16 is more acutely angled in comparison to the pointed front end 15 thereby facilitating positioning of an opened fluid housing operable door on such top end 16 (so as to retain the opened operable door in an open position). In some embodiments, the width of the opener element 8 is sufficiently narrow so as to retain a hollow passage within the interior of the main body 2. In some embodiments, the width of the opener element 8 is sufficiently narrow so as to facilitate (e.g., not hinder) the passage of a fluid through the interior of the main body 2 to the applicator 3.

Referring to FIG. 3, a fluid housing 9 is shown positioned within the interior of the main body 2 from the main body proximal end 4 to the vicinity of the main body mid portion 6 just prior to the opener element 8.

Figure 4:
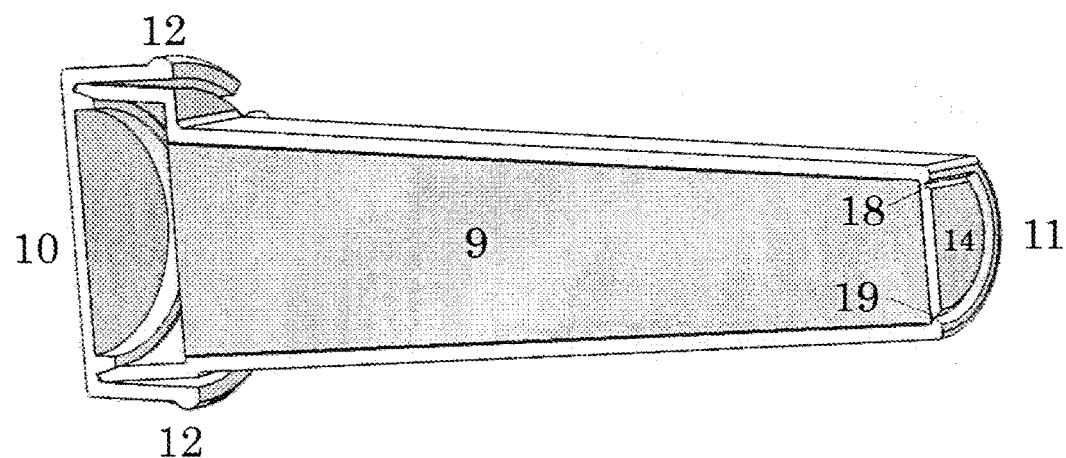
FIG. 4 shows a fluid housing embodiment of the present invention.

FIG. 4 shows a fluid housing 9 separated from the apparatus. Generally, the fluid housing 9 is configured to store a fluid without risk of unintentional fluid release.

As shown in FIGS. 3 and 4, the fluid housing 9 has a fluid housing proximal end 10 and a fluid housing distal end 11. In some embodiments, the fluid housing proximal end 10 and fluid housing distal end 11 are closed, thereby enabling the fluid housing 9 to securely store a fluid. In some embodiments, as shown, the fluid housing proximal end 10 has thereon one or more fluid housing proximal end lips 12 for purposes of preventing unintentional movement of the fluid housing 9 while positioned within the main body 2 (see FIG. 3) (described in more detail below).

Still referring to FIGS. 3 and 4, the fluid housing 9 is not limited to a particular shape. In some embodiments, the shape of the fluid housing 9 is such that it is able to be positioned within the main body of the apparatus 2 from the main body proximal end 4 to the main body mid portion 6 just prior to the opener element 8. In some embodiments, the fluid housing 9 is positioned within the main body 2 such that the fluid housing proximal end 10 does not extend beyond (e.g., outside) the main body proximal end rim 5 (thereby preventing unintentional depression of the fluid housing into the main body resulting in unintentional release of its fluid).

In some embodiments, the fluid housing 9 is positioned within the main body 2 such it may not be removed without damaging the apparatus and/or fluid housing. In some embodiments, the fluid housing 9 is removable from the main body 2. For example, in some embodiments, the fluid housing 9 may be inserted into the main body 2 or removed from the main body 2.

Referring to FIG. 3, the interior of the main body proximal end 4 has one or more main body proximal end recesses 13. The main body proximal end recesses 13 are not limited to a particular positioning within the main body proximal end 4. In some embodiments, the one or more main body proximal end recesses 13 are configured to receive the fluid housing proximal end lips 12 for purposes of preventing unintentional movement of the fluid housing 9 while positioned within the main body 2 (shown in FIG. 3). Such retention, however, may be overcome through application of a distally directed force upon the fluid housing proximal end 4 (e.g., thereby "pushing" the fluid housing proximal end lips 12 past the main body proximal end recesses 13). The main body proximal end recesses 13 are not limited to a particular shape. In some embodiments, the shape of the main body proximal end recesses 13 are curved so as to facilitate engagement and non-engagement with fluid housing proximal end lips 12.

Referring to FIGS. 3 and 4, the fluid housing distal end 11 is closed with a fluid housing distal end operable door 14. The present invention is not limited to a particular type or kind of fluid housing distal end operable door 14.

Referring to FIGS. 3, 4 and 5, in some embodiments, the fluid housing proximal end 10 has an operable door 14. The embodiments are not limited to a particular operable door 14. In some embodiments, the operable door 14 is hinge based such that it is configured to be opened. In some embodiments, the operable door 14 is peel hinge based such that it is configured to be opened. In some embodiments, as shown in FIGS. 3, 4 and 5, the operable door 14 has an operable door top peel portion 18 and an operable door bottom peel portion 19. In some embodiments, the operable door top peel portion 18 and the operable door bottom peel portion 19 have different degrees of thickness. In some embodiments, the thickness of the operable door bottom peel portion 19 is such that upon engagement with the opener element pointed front end 15 (see FIGS. 3 and 5) the operable door bottom peel portion 19 will detach (e.g., opens). In some embodiments, the thickness of the operable door top peel portion 18 is thick enough to bend without detaching (e.g., thereby operating as a hinge (e.g., a swinging hinge)) as the operable door bottom peel portion 19 detaches. As such, in some embodiments, the operable door 14 is configured to open via detachment of the operable door bottom peel portion 19 and flexing of the operable door top peel portion 18 in response to engagement with the opener element pointed front end 15. Accordingly, in some embodiments, depression of the fluid housing proximal end 10 (e.g., by a user) causes the fluid housing 9 to distally advance through the interior of the main body 2 resulting in engagement between the fluid housing operable wall 14 and the opener element pointed front end 15. Such engagement between the fluid housing operable wall 14 and the opener element pointed front end 15 results in contacting of the opener element pointed front end 15 with the operable wall bottom peel portion 19 such that the operable wall bottom peel portion 19 detaches, and as the opener element 8 advances into the fluid housing 9 (e.g., thereby opening the operable door), the operable door top peel portion 18 flexes and rests upon the opener element top end 16 (thereby retaining the operable door 14 in an open position). In some embodiments, such opening of the operable door 14 results in a release of the fluid housing contents (e.g., fluid) through the opened operable door 14, into the interior of the main body 2 (e.g., the main body mid portion 6 and main body distal end 7), and ultimately into the applicator 3. In some embodiments, the entire contents of fluid housing 9 are thereby transferred to the applicator 3, which may thereby be used to apply such contents to a subject. In some embodiments, the operable door top peel portion 18 and the operable door bottom peel portion 19 are formed through a coining process.

As shown in FIG. 3, the fluid housing proximal end 10 is flush or recessed relative to the main body proximal end rim 5. This provides the advantage of preventing accidental actuation of the fluid housing 2 prior to use (e.g., unintentional depression of the fluid housing proximal end 10 such that the fluid housing operable door 14 is opened thereby releasing its contents) (e.g., during shipping, handling and/or storage). In some embodiments, the main body proximal end 4 comprises a cap or seal over the main body proximal end rim 5 to protect the contents and maintain the seal of fluid housing 2. In some embodiments, the fluid housing proximal end 10 comprises a cap or seal to protect the contents and maintain the seal of fluid housing 2.

As shown in FIG. 3, in some embodiments, the shape of the main body mid portion 6 is narrowed (in comparison to the main body proximal portion 4) so as to prevent movement of the fluid housing 9 beyond the main body mid portion 6 (e.g., the width or radius of the main body mid portion 6 is smaller or less than the radius of the fluid housing distal end 11).

In some embodiments, the fluid housing is filled with a medicant, cleaning solution or the like. Such medicants are inclusive of antiseptic solutions, sterilizing solutions, etc., in liquid or in gel form. The present invention is not limited to a particular fluid for dispensing by the apparatus. In some embodiments, the fluid is a medical fluid (e.g., comprising a medicament). In some embodiments, the fluid is a sterilizing fluid (e.g., those described in copending application Ser. No. 13/621,645; herein incorporated by reference in its entirety or commercial solutions such as Excel-AP, manufactured by Aplicare, Branford Conn.).

The components of medical skin apparatus may be fabricated from materials suitable for medical applications, such as, for example, polymerics or metals, such as stainless steel, depending on the particular application and/or preference of a user. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

In some embodiments, fluids are added during manufacture and the apparatus is shipped to a user containing the fluid in the fluid housing. In other embodiments, the apparatus is provided to a user empty and the user adds the fluid prior to use. In some embodiments, the apparatus is intended for a single use and is disposed after use. In other embodiments, the apparatus can be refilled and used multiple times.

The apparatus described herein finds use in any number of applications involving medical (e.g., human medical setting or veterinary setting) or other uses of fluids applied to surfaces of a subject. In some embodiments, a sterilizing fluid is applied to a surface (e.g., skin or external membrane) of a subject prior to a medical procedure, such as, for example, surgical, diagnostic and related treatments of diseases and body ailments of a subject. It is further envisioned that the principles relating to the skin applicator apparatus disclosed include application of various agents to a body, such as, for example, medications and other fluids.

The present invention is not limited to a particular subject. In some embodiments, the subject is a human. In some embodiments, the subject is a non-human animal (e.g., a non-human mammal). In some embodiments, the subject is any animal seen in a veterinary setting (e.g., cat, dog, bird, turtle, rabbit, snake, etc.).

As described above, the applicator apparatus of the present disclosure includes key features and advantages not found in existing applicators. For example, positioning of the fluid housing proximal end rim recessed or flush relative to the main body proximal end rim prevents accidental actuation of the fluid housing prior to use of the apparatus (e.g., during manufacture, shipment, handling, and/or storage of the apparatus). In addition, use of an opener element and operable door as described herein for release of a fluid within the fluid housing ensures a more reliable fluid release in comparison to alternate previous designs.

In alternate embodiments, the fluid housing is a fractionable ampoule. In such embodiments, depressing of the fluid housing causes movement of the fluid housing in a distal manner and a fractioning of the ampoule upon contact with the opener element resulting in release of the fluid within the fluid housing. Such release of the fluid results in its progression through the main body and ultimately into the applicator.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

We claim:

1. An apparatus for applying a fluid, consisting essentially of
   a hollow main body having an open main body proximal end, a main body mid portion, and an open main body distal end, wherein said interior of said main body mid portion has therein an opener element,
   an applicator component, and
   a fluid housing having a closed fluid housing proximal end and a fluid housing distal end having a fluid housing operable door, wherein the fluid housing operable door has therein a bottom portion peeled element and a top portion peeled element, wherein the top portion peeled element is thicker than the bottom portion peeled element;
   wherein said main body distal end is engaged with said applicator component,
   wherein said fluid housing is positioned within the interior of the main body such that the fluid housing operable door is positioned in the vicinity of the opener element such that a distal movement of the fluid housing will result in an insertion of the opener element into the fluid housing operable door thereby releasing the contents of the fluid housing into interior of the main body and into the applicator component,
   wherein said insertion of the opener element into the fluid housing operable door involves a detachment of the bottom portion peeled element and a flexing of the top portion peeled element such that the operable door engages the opener element and remains open,
   wherein said fluid housing proximal end has thereon fluid housing proximal end lips,
   wherein the main body proximal end has thereon main body proximal end recesses,
   wherein said fluid housing is positioned within the interior of the main body such that the fluid housing proximal end lips are positioned within the main body proximal end recesses, wherein said positioning of said fluid housing proximal end lips within the main body proximal end recesses prevents unintentional movement of the fluid housing positioned within the main body,
   wherein said fluid housing is positioned within the interior of the main body such that at least a portion of the fluid housing proximal end is flush or recessed relative to the main body proximal end.

2. The apparatus of claim 1, the top portion peeled element operate as a flexible hinge as the opener element inserts into the fluid housing operable door.

3. The apparatus of claim 1, wherein said fluid housing houses a fluid.

4. The apparatus of claim 3, wherein said fluid is a medicament fluid or a sterilizing fluid.

5. The apparatus of claim 1, wherein said applicator component is an absorbent sponge or pad.

6. The apparatus of claim 1, wherein said applicator component has a shape selected from the group consisting of round, oval, square, triangular, and tear-drop.

7. The apparatus of claim 1, wherein said fluid housing is positioned within the interior of the main body such that the fluid housing proximal end is flush or recessed relative to at least a portion of the main body proximal end.

8. A method of applying a fluid to a subject, comprising:
   a) providing the apparatus of claim 1 having fluid within said fluid housing onto a surface of a subject; and
   b) causing insertion of said opener element into said fluid housing operable door thereby evacuating said fluid within said fluid housing into the interior of said main body and through said applicator onto said surface of said subject.

9. The method of claim 8, wherein said surface of said subject is skin.

10. The method of claim 8, wherein said subject is a human animal.

11. The method of claim 8, wherein said subject is a non-human animal.

12. An apparatus for applying a fluid, consisting essentially of
    a hollow main body having an open main body proximal end, a main body mid portion, and an open main body distal end, wherein said interior of said main body mid portion has therein an opener element,
    an applicator component, and
    a fluid housing having a fluid housing proximal end and a closed fluid housing distal end, wherein a cap or seal positioned onto the fluid housing proximal end, wherein the fluid housing distal end has therein a bottom portion peeled element and a top portion peeled element, wherein the top portion peeled element is thicker than the bottom portion peeled element;
    wherein said main body distal end is engaged with said applicator component,
    wherein said fluid housing is positioned within the interior of the main body such that the bottom portion peeled element and a top portion peeled element are positioned in the vicinity of the opener element such that a distal movement of the fluid housing will result in an insertion of the opener element into the bottom portion peeled element and a top portion peeled element thereby releasing the contents of the fluid housing into interior of the main body and into the applicator component, wherein said insertion of the opener element into the bottom portion peeled element and a top portion peeled element involves a detachment of the bottom portion peeled element and a flexing of the top portion peeled element such that the fluid housing distal end engages the opener element and remains open, wherein said fluid housing is positioned within the interior of the main body such that at least a portion of the fluid housing proximal end is flush or recessed relative to the main body proximal end.

13. The apparatus of claim 12, wherein said fluid housing is positioned within the interior of the main body such that the fluid housing proximal end is flush or recessed relative to at least a portion of the main body proximal end.

* * * * *